United States Patent [19]

Ingrahm et al.

[11] Patent Number: 5,602,030

[45] Date of Patent: Feb. 11, 1997

[54] RECOMBINANT GLUCOSE UPTAKE SYSTEM

[75] Inventors: Lonnie O. Ingrahm, Gainesville, Fla.; Jacob L. Snoep, Groede; Nico Arfman, Delft, both of Netherlands

[73] Assignee: University of Florida Research Foundation, Gainesville, Fla.

[21] Appl. No.: 218,914

[22] Filed: Mar. 28, 1994

[51] Int. Cl.$^6$ .............................. C12N 9/12; C12N 15/54; C12N 1/21; C12N 15/63

[52] U.S. Cl. ..................... 435/252.3; 435/69.1; 435/194; 435/252.33; 435/254.1; 435/254.11; 435/255.1; 435/255.2; 435/320.1

[58] Field of Search ................................... 435/69.1, 194, 435/252.3, 252.33, 254, 320.1, 254.1, 254.11, 255.1, 255.2

[56] References Cited

PUBLICATIONS

Ko et al., "Roles of Multiple Glucose Transporters in *Saccharomyces cerevisiae*," Molecular and Cellular Biology, Jan. 1993 vol. 13, No. 1, pp. 638–648.

Fukuda et al., "Cloning of Glucose Phosphorylating Genes in *S. cerevisiae* by the KU–Method and Application to ATP Production," Agric. Biol. Chem. vol. 48, No. 11, pp. 2877–2881, 1984.

Bisson et al., "Involvement of kinases in glucose and fructose uptake by *Saccharomyces cerevisiae*," Proc. Natl. Acad. Sci. USA, vol. 80, pp. 1730–1734, Mar. 1983.

Barnell, et al. *Jrnl. of Bacteriology*, "Sequence and Genetic Organization of a *Zymomonas mobilis*. . . ", 172:7227–7240 (Dec. 1990).

Fukuda et al. *Jrnl. of Bacteriology*, "Cloning of the Glucokinase Gene in *Escherichia coli* B", 156:922–925 (Nov. 1983).

Curtis et al. *Jrnl. of Bacteriology*, "Phosphorylation of D–Glucose in *Escherichia coli* Mutants Defective in . . . ", 122:1189–1199 (Jun. 1975).

Erni *FEMS Microbiology Reviews*, "Glucose transport in *Escherichia coli*", 63:13–24 (1989).

Postma "Phosphotransferase System for Glucose and . . . " in *Escherichia Coli and Salmonella Typhimurium: Cellular and Molecular Biology*, Neidhardt et al. (eds.) pp. 127–141 (1987).

Meadow et al. *Annu. Rev. Biochem.*, "The Bacterial Phosphoenolpyruvate: Glucose Phosphotransferase System", 59:497–542 (1990).

*Primary Examiner*—Dian C. Jacobson
*Assistant Examiner*—Hyosuk Kim
*Attorney, Agent, or Firm*—Hamilton, Brook, Smith & Reynolds, P.C.

[57] ABSTRACT

Recombinant organisms are disclosed that contain a pathway for glucose uptake other than the pathway normally utilized by the host cell. In particular, the host cell is one in which glucose transport into the cell normally is coupled to PEP production. This host cell is transformed so that it uses an alternative pathway for glucose transport that is not coupled to PEP production. In a preferred embodiment, the host cell is a bacterium other than Z. mobilis that has been transformed to contain the glf and glk genes of Z. mobilis. By uncoupling glucose transport into the cell from PEP utilization, more PEP is produced for synthesis of products of commercial importance from a given quantity of biomass supplied to the host cells.

10 Claims, 1 Drawing Sheet

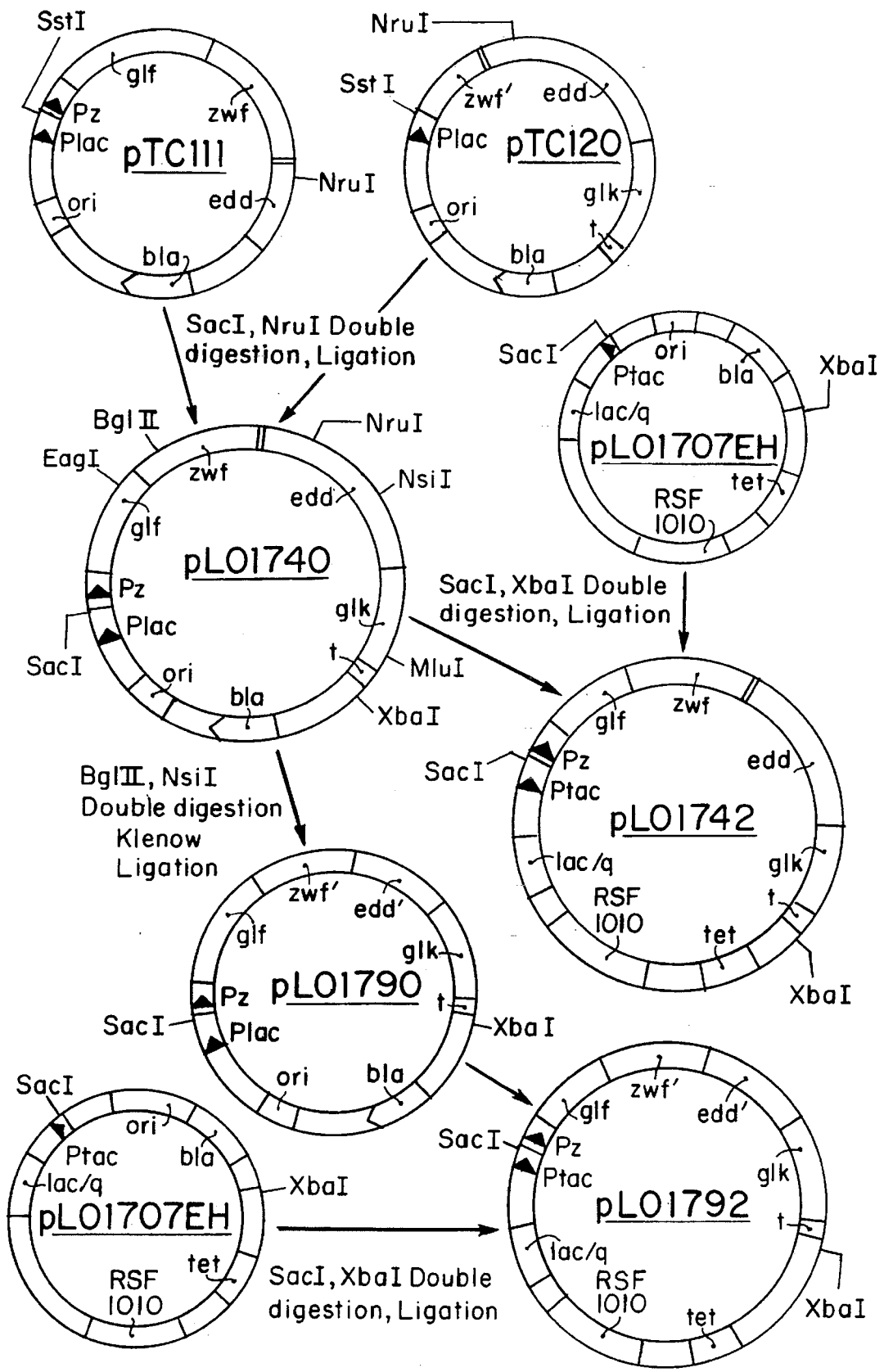

RECOMBINANT GLUCOSE UPTAKE SYSTEM

The present invention was made with government support provided, through the Florida Agricultural Experiment Station, under USDA Alcohol Fuels Program grants Nos. 86CRCR12134, 88-37233-3987 and under DOE Office of Basic Energy grant FG05-86ER13574. The federal government has certain rights in the present invention.

BACKGROUND OF THE INVENTION

The present invention relates to a recombinant organism that expresses heterologous DNA coding for the elements of an alternative pathway for glucose uptake, in particular, a pathway utilized in nature by Zymomonas mobilis.

The cost of microbial production of chemicals is typically dominated by the cost of the sugar feedstock. Glucose is a basic starting point for the microbial production of commercial products such as amino acids, vitamins, citrate, succinate, fumarate, citrate, lactic acid, acetic acid, ethanol and solvents. Processes for production of various chemicals from glucose strive to maximize the efficiency with which the carbon skeleton of glucose is converted into the desired product.

Phosphoenol pyruvate (PEP) is a central intermediate in glucose metabolism, residing at a branch point for the biosynthesis of many compounds of commercial importance. For example, an equimolar amount PEP is combined with erythrose-4-phosphate to provide the carbon skeleton for aromatic products such as tyrosine, phenylalanine, tryptophan, and some vitamins among other compounds. PEP also is combined with carbon dioxide to produce oxaloacetic acid in the Tricarboxylic Acid (TCA) Cycle. Oxaloacetic acid serves as the carbon skeleton for aspartic acid, asparagine, threonine, isoleucine, methionine, diaminopimelic acid, lysine, pyrimidines, and a host of intermediates. By a reverse of the TCA cycle, oxaloacetic acid is converted to fumarate and succinate. Succinate serves as the carbon backbone for tetrapyrrole biosynthesis. In the forward TCA cycle, oxaloacetic acid is combined with acetyl-CoA to form citric acid, α-ketoglutarate and succinate among other intermediates. α-Ketoglutarate serves as the primary carbon skeleton for the synthesis of glutamic acid, ornithine, arginine, citrulline, polyamines, and glutamine and many intermediates. Thus, the conversion of PEP to oxaloacetic acid serves as a primary route to supply TCA Cycle intermediates which can be used for biosynthesis. In many bacteria, PEP also is necessary for the transport of glucose into the cell. Glucose is phosphorylated in a concerted process by a multiprotein, -membrane-bound complex termed the phosphotransferase system (PTS). In this process, PEP serves as the source of a high energy phosphate which is ultimately attached to glucose to yield glucose-6-phosphate and pyruvate. During glycolysis in these organisms, half of the PEP produced is obligately consumed to provide energy for glucose uptake. This reduces by 50% the amount of PEP available as a source of carbon skeletons for biosynthesis, severely impacting the efficiency of conversion into many desired commercial products.

The ethanol-producing bacterium Z. mobilis has an alternative mechanism for glucose uptake that utilizes ATP rather than PEP as an energy source. In this organism, glucose selectively enters via a membrane permease, designated "glucose-facilitated diffusion protein" (GLF), which has a deduced size of approximately 50 kilodaltons (kDa). The intracellular glucose subsequently is phosphorylated by a glucose-specific hexokinase called glucokinase (GLK) using ATP to produce glucose-6-phosphate and ADP. This glucose-6-phosphate is chemically identical to the glucose-6-phosphate produced by the PTS pathway. A similar alternative pathway exists in yeast, although the hexokinase of yeast is not glucose-specific.

Although Z. mobilis has simple nutritional requirements, the range of sugars metabolized by this organism is very limited and normally consists of glucose, fructose and sucrose. Zymomonas mobilis is incapable of growth without a fermentable sugar, even in rich medium such as nutrient broth. Substrate-level phosphorylation from the fermentation of these simple sugars is the sole source of energy for biosynthesis and homeostasis. That is, Z. mobilis is an obligately fermentative bacterium which lacks a functional system for oxidative phosphorylation. In the absence of a functioning electron transport system for oxidative phosphorylation, a large proportion of the PEP produced is consumed in short pathways which regenerate $NAD^+$, an obligate requirement for continued glycolysis and ATP production. In addition to being an obligatively fermentative bacterium that is limited with respect to the variety of feedstocks that it can metabolize, Z. mobilis also tends to be a relatively demanding organism in terms of culture conditions.

Recently, Barnell et al. cloned and sequenced the Z. mobilis GLKgene (glk) and showed it to be expressed in an active form in E. coli, J. Bacteriol. 172:7227 (1990). A 1,422 base pair open reading frame, characterized by partial homology with both the xylose permease gene in E. coli and a human glucose transporter, also was discovered, approximately 3 kilobase pairs upstream from the glk gene. It was hypothesized that this open reading frame corresponded to the structural sequence of the Z. mobilis GLF gene (glf). Production of GLF in recombinant E. coli was not observed by Barnell et al., however, and a plasmid containing both the glk and glf genes was not constructed.

Prior to the present invention, it would have been doubtful whether the GLF gene would express functional protein in an organism other than Z. mobilis. Unlike soluble cytoplasmic enzymes that have been readily expressed as functional proteins in E. coli, a membrane permease protein must be correctly inserted into the cytoplasmic membrane and form integral interactions with the membrane lipids to ensure function. The expression of functional membrane proteins in heterologous systems is problematic. Although function occurs in some cases, heterologous membrane proteins often fail to function in E. coli. Failure to function is presumed to be due in part to differences between signal sequences for membrane insertion and differences in membrane lipid compositions. Barnell et al. do not suggest or provide any evidence that the glf-encoded protein was functional in E. coli.

Zymomonas mobilis has a unique membrane lipid composition. It has been hypothesized that this composition represents an evolutionary adaptation that allows Z. mobilis to survive in the presence of high levels of ethanol. This membrane composition in Z. mobilis is very different from that of other microorganisms, including microbes like E. coli and other enteric bacteria, a factor militating against insertion of membrane proteins into E. coli. For example, Z. mobilis contains different phospholipids than E. coli. Positively charged phosphatidyl choline is abundant in Z. mobilis, but totally absent in E. coli. Phosphatidyl choline is synthesized from phosphatidyl ethanolamine, a conversion that forms the basis for many metabolic control systems in eukaryotic organisms.

The membrane phospholipids of Z. mobilis also differ with respect to the fatty acid composition. In Z. mobilis, the fatty acid composition is almost exclusively 18:1 vaccenic acid. In contrast, E. coli phospholipids contain a mixture of shorter chain saturated and unsaturated fatty acids which change in response to growth temperature as a part of the temperature adaptation process.

An additional feature unique to Z. mobilis is the presence of abundant hopanoids. Hopanoids either are present at very low levels or are absent in E. coli. Hopanoids have been proposed to serve as steroid equivalents in prokaryotic membranes and are hypothesized to be important for ethanol tolerance in Z. mobilis. Another unique class of membrane lipids in Z. mobilis is the ceramides. Ceramides are common in eukaryotes but are very unusual in bacteria. Thus, many differences exist in membrane compositions of Z. mobilis and E. coli which may be related to their respective ranges of environmental tolerance.

Molecular genetics offers the potential to combine in a single organism the ability to metabolize efficiently the entire range of biomass-derived sugars with the ability to use a pathway for glucose uptake that is not obligately coupled to PEP. For example, by modifying an enteric bacteria such as E. coli to use an alternative pathway for glucose uptake characteristic of Z. mobilis, the output of any synthetic product derived from a PEP precursor could be doubled because glucose transport into the cells would not be obligately coupled to PEP. As discussed above, there have been reasons to doubt heretofore that a recombinant organism containing the glf gene would exhibit the alternative pathway for glucose transport because of the significant differences between the membrane lipid composition of Z. mobilis and other organisms.

SUMMARY OF THE INVENTION

It is therefore an object of the present invention to provide a recombinant organism in which glucose uptake is not obligately coupled to PEP production, in particular a recombinant organism containing heterologous DNA segments encoding glucose-facilitated diffusion protein and glucokinase.

It is a further object of the invention to provide a process for producing such a recombinant organism.

In achieving these and other objects there has been provided in accordance with one aspect of the present invention a recombinant host cell which functionally expresses heterologous DNA that encodes glucose-facilitated diffusion protein and a hexokinase, that is, a recombinant host cell that expresses protein that is correctly inserted into the cytoplasmic membrane and that forms integral interactions with the membrane lipids to ensure function. In a preferred embodiment, the DNA encodes Z. mobilis glucose-facilitated diffusion protein and Z. mobilis glucokinase and is under transcriptional control of a promoter which is endogenous to said host cell. The recombinant host cell additionally may comprise heterologous DNA encoding Z. mobilis glucose-6-phosphate dehydrogenase and/or heterologous DNA encoding Z. mobilis 6-phosphogluconate dehydratase.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURE

The FIGURE is a diagram of shuttle vectors according to the present invention.

DETAILED DESCRIPTION OF THE PREFERRED EMBODIMENT

The present invention relates to a recombinant organism containing a pathway for glucose uptake other than the pathway normally utilized by the host cell. In particular, the host cell is one in which glucose transport into the cell is normally coupled to PEP production. This host cell is transformed to contain heterologous DNA that encodes an alternative pathway for glucose transport into the cell that is not coupled to PEP production. The alternative pathway includes GLF and a hexokinase, an enzyme having the ability to phosphorylate glucose and other six-carbon sugars using ATP.

A number of organisms possess such an alternative pathway for glucose transport into cells. Exemplary of such organisms are Z. mobilis and yeast species such as Saccharomyces cerevisiae. Humans also possess this pathway. These organisms possess genes that encode a glucose-facilitated diffusion protein and a hexokinase. In Z. mobilis the hexokinase is a glucokinase, a glucose-specific hexokinase. In yeasts, on the other hand, the hexokinase is not glucose-specific.

In any event, the existence of this alternative pathway can be readily detected by transport studies with different levels of glucose, as described in Dimarco and Romano, *Appl. Environ. Microbiol.* 51:197–200 (1985).

In the present context, "heterologous" DNA segment refers to a DNA segment from an organism that is different than the host cell. This heterologous DNA can be incorporated into a plasmid or other vector. Alternatively, this DNA can be incorporated into the chromosomal DNA of the host organism, as disclosed in co-pending application Ser. No. 07/624,227, filed Dec. 7, 1990, the contents of which are incorporated herein by reference.

Surprisingly, it has been discovered that host cells containing heterologous DNA segments relating to membrane-associated glucose uptake are functional despite significant differences between the membrane lipid composition of the host organism and the organism from which the heterologous DNA segments arise. By uncoupling glucose transport into the cell from PEP production, more PEP for synthesis of products of commercial importance is produced from a given quantity of biomass supplied to the host cells.

Suitable host cells according to the present invention include any cells into which a heterologous DNA segment can be inserted. Illustrative of such hosts would be eukaryotic cells, such as animal cells, insect cells, fungal cells, yeasts and bacteria, for example, enteric bacteria. In addition to E. coli, other enteric bacteria of the genera Erwinia, like E. chrysanthemi, and Klebsiella, like K. planticola and K. oxytoca, are particularly attractive hosts because they can utilize a variety of sugars, including pentoses and lactose. Advantageous hosts can also be selected from the broader category of gram-negative bacteria, such as species of the genus Xanthomonas, and from the gram-positive bacteria, such as members of the genus Bacillus, Clostridium and Cellulomonas. Appropriate transformation methodology is available for each of these different types of hosts.

According to the present invention, the heterologous genes are expressed at levels that facilitate the transport of glucose into the host cell by the alternative pathway for glucose transport and subsequent phosphorylation using ATP. By virtue of the insertion of these genes into the host, an organism in which glucose uptake by cells is normally obligately coupled to PEP production is transformed so that glucose uptake proceeds via the alternative pathway.

The heterologous genes can be cloned in a conventional manner by complementation of host cell mutants with specific defects in glucose metabolism, according to techniques described in Barnell et al., supra, the contents of which are incorporated herein by reference. For example, in order to clone the gene for glucokinase, a library of genomic DNA from the organism having the alternative pathway for glucose transport is transformed into a host cell mutant that is defective in the PTS system for glucose and mannose uptake and also carries a defect in glucokinase. Such a host cell mutant forms white colonies on MacConkey agar plates. The library is screened for the glucokinase gene by conversion of the host cell mutant to formation of pink colonies on the glucose-MacConkey agar. In some cases, this pink is observed only after prolonged incubation, indicating a very weak positive reaction. Pink colonies are assayed for glucokinase activity.

GLF cannot be assayed alone. However, clones expressing both glk and glf give a very bright red reaction on glucose-MacConkey within a few hours, indicating a very strong reaction.

Alternatively, the proteins encoded by the genes can be isolated and purified. Oligonucleotide probes then can be constructed to clone the corresponding genes.

Once the genes are obtained, they can be used to transform the host cell, although other methods of gene transfer may be used also, such as conjugation, transduction and electroporation. Transformation can be effected by means of a vector. Alternatively, the gene can be incorporated into the chromosomal DNA of the host organism, as mentioned above. If a vector is used for transformation, it is preferably a plasmid, although other vectors such as lambda phage vectors, cosmids and phagemids also can be used. The genes encoding the alternative pathway for glucose transport are cloned into a suitable vector, which is then inserted into the host cell.

The heterologous DNA segments are inserted into the shuttle vector so that they are under the transcriptional control of an endogenous promoter. For example, when the host cell is a strain of *E. coli*, the tac promoter of *E. coli* can be used. Although the heterologous segments are integrated into the vector on the downstream (3') side of the promoter, promoter activity may also be supplied from native genes after chromosomal integration.

In a preferred embodiment, the heterologous DNA segments are obtained from *Z. mobilis* and correspond to the genes encoding GLF and GLK. The glf and glk genes are cloned into an *E. coli/Z. mobilis* shuttle vector and used to transform the *E. coli* host cell.

The minimal coding regions with ribosomal binding sites for glk and glf can be synthesized via the polymerase chain reaction (PCR), using *Z. mobilis* chromosomal DNA as a template. Restriction sites at both the 3' and 5' ends of the genes allow the directional insertion of the PCR products into a vector oriented to allow transcription from a promoter.

In a preferred embodiment, a nucleotide sequence encoding a selectable marker gene also is cloned into the shuttle vector. For example, a selectable marker gene conferring resistance to a particular antibiotic may be used.

Plasmids can be constructed that contain each gene separately, under the control of separate promoters. It is preferred, however, to construct a plasmid that contains both genes together, under the control of a single promoter, and use that to transform the host cell. The ability of a glucose-negative *E. coli* mutant to grow rapidly on glucose as the sole carbon source can be restored by this introduction of the alternative pathway for glucose transport, demonstrating that the glf and glk genes function in *E. coli* to provide an alternative pathway for glucose uptake.

The expression of glk- and glf-encoded proteins can be examined by sodium dodecyl sulfate-polyacrylamide gel electrophoresis. The expression of GLK, the enzyme encoded by glk, can also be determined by an enzyme assay. No direct enzymatic test is available for the quantification of the glf-encoded gene product, but expression of active protein can be established by demonstration of function in glucose-negative mutants.

By using ATP rather than PEP as a source of energy for glucose transport, the net production of PEP molecules in *E. coli* can be doubled by the exclusive use of the *Z. mobilis* glucose uptake pathway. This doubling of PEP availability dramatically improves the stoichiometry of manufacturing many microbial products from glucose. Addition of this alternative *Z. mobilis* pathway to *E. coli* that contains a functional, native PTS pathway increases the rate of glucose uptake and the production of a useful product.

The present invention can further be understood with reference to the following examples, illustrating introduction of *Z. mobilis* glk and glf genes for glucose uptake into a strain of *E. coli*. Exemplified bacterial strains and plasmids are summarized in Table 1. *E. coli* strains were grown at 37° C. in Luria broth, as disclosed in Fritsch et al., MOLECULAR CLONING: A LABORATORY MANUAL (2nd ed.), Cold Spring Harbor Laboratory (N.Y. 1989), unless otherwise noted. *Zymomonas mobilis* was grown at 30° C. in complex medium as previously described in Byun et al., J. Ind. Microbiol. 1:9–15 (1988). When appropriate, tetracycline (10 mg/liter) or ampicillin (50 mg/liter) were included for selection.

Growth experiments were performed in 250 ml Erlenmeyer flasks containing 40 ml of media in a reciprocating water bath (about 80 oscillations/min; 37° C.). Overnight cultures grown in Luria broth were harvested, washed in minimal medium and used as inocula to provide an initial optical density of 0.1 at 550 nm. Growth was monitored spectrophoto-metrically at 550 nm with a Spectronic 70 spectro-photometer (Bausch & Lomb, Inc., Rochester, N.Y.).

In order to assay for enzyme, cells were grown overnight in Luria broth in the presence or absence of 1 mM isopropyl β-D-thiogalactopyranoside (IPTG). Cultures were harvested by centrifurgation (6,000×g, 10 min). The resulting cell pellet was washed and resuspended in 20 mM morpholine ethanesulfonic acid (MES)-KOH pH 6.5 containing 2 mM magnesium chloride, 50 mM sodium chloride and 10 mM β-mercaptoethanol. After disruption in a French pressure cell, specific activities of NAD-dependent glucose-6-phosphate dehydrogenase (GDH), 6-phosphogluconate dehydratase (GDT), and glucokinase (GLK) were determined using the Bradford assay for protein estimation. See Scopes et al. Biochem. J. 228:627–634 (1985); Lessie et al. *J. Bacteriol.* 93:1337–1345 (1967); Doelle *Eur. J. Appl. Microbiol. Biotechnol.* 14:241–246 (1982); Bradford *Anal. Biochem.* 72:248–254 (1976).

Bacterial strains and plasmids referenced in the following examples are summarized in Table 1.

TABLE 1

Exemplified strains and plasmids

| Strain or plasmid | Relevant characteristics |
|---|---|
| *E. coli* K-12 strains | |
| DH5α | thi lacZΔM15 recA nal$^r$ |
| ZSC113 | glucose negative mutant of *E. coli* K12 (lacZ82 ptsM12 ptsG22glk-7 rha-4 rpsL223) |
| Plasmids | |
| pUC18 | bla lacI'Z'$^b$ |
| pMMB66EH | RSF1010Δ[PstI-PvuII 2.87 kb] Ω[(lacI$^q$ tacP rrnB bla NruI-AhaIII 3.0 kb]; Ap$^r$ |
| pBR322 | bla tet |
| pTC111 | Barnell et al. (1990), op. cit. |
| pTC120 | Barnell et al. (1990), op. cit. |
| pLOI740 | The FIG. |
| pLOI744 | pTC111 with frame shift mutation in glf |
| pLOI746 | pTC120 with frame shift mutation in glk |
| pLOI790 | The FIG. |
| pLOI142 | pUC18 containing NotI-polylinker in SmaI Site |
| pLOI704EH | pMMB66EH with pUC18 EcoRI-HindIII polylinker |
| pLOI705EH | pLOI704EH containing NotI site |
| pLOI706EH | pLOI705EH containing a 1.43 kb EcoRI-Ava Itet fragment from pBR322 in the PvuI site within bla; Tc$^r$ Ap$^s$ |
| pLOI707EH | The FIG. - pLOI706EH fused to pLOI142 (SstI-NotI); Tc$^r$ Ap$^r$ |
| pLOI742 | The FIG. - pLOI706EH containing glf, zwf, edd, glk genes; Tc$^r$ Ap$^s$ |
| pLOI763 | pLOI706EH containing Z. *mobilis* promoter; zwf, edd, glk genes; Tc$^r$ Ap$^s$ |
| pLOI767 | pLOI706EH containing Z. *mobilis* promoter; glf, zwf, edd genes; Tc$^r$ Ap$^s$ |
| pLOI792 | FIG. 1 - pLOI706EH containing Z. *mobilis* promoter; glf, glk genes; Tc$^r$ Ap$^s$ |
| pLOI670 | derivative of pLOI142 that contains only the coding region and ribosomal-binding site for glf |

$^b$Incomplete lacI and incomplete lacZ.

Cultures of *E. coli* harboring pLOI792 and pLOI790 have been deposited with the American Type Culture Collection (ATCC), 12301 Parklawn Drive, Rockville, Md., 20852, USA. The deposits have been assigned accession numbers ATCC 65986 and ATCC 65987, respectively. It should be understood, however, that the subject cultures are not necessary to practice the present invention. Nor does availability of the deposit constitute a license to practice the subject invention in derogation of patent rights granted by governmental action.

Example 1 PLASMID CONSTRUCTION AND TRANSFORMATION OF *E. COLI*

Plasmid pMMB66EH is a broad host range expression vector that contains an RSF1010 replicon, tac promoter, lacI$^q$ repressor, and the bla gene as a selectable marker. See Fürste et al. *Gene* 48:119–131 (1986) and Frey et al. 79–94. In C. M. Thomas (ed.), Promiscuous plasmids of Gram-negative bacteria. Academic Press, Inc., New York (1989). This vector contains an EcoRI-HindIII polylinker fragment for cloning, flanked at the 5'-end by the tac promoter and at the 3'-end by two strong transcriptional terminators from the rrnB gene. The polylinker region was modified to contain unique SstI and NotI sites (NotI linker obtained from New England Biolabs, Beverly, Mass.).

The EcoRI-HindIII polylinker present in pMMB66EH was replaced by the EcoRI-HindIII polylinker from pUC18 (obtained from Pharmacia LKB Biotechnology Inc., Piscataway, N.J.) to form pLOI704EH, resulting in the introduction of unique SstI and SmaI sites. Next, the 12 bp SstI-SmaI fragment of pLOI704EH was replaced by the 40 bp NotI-containing SstI-SmaI polylinker fragment derived from pBluescript II SK$^+$ to form pLOI705EH. A tet gene was added to facilitate selection. This tet gene was isolated on the 1,427 bp EcoRI-AvaI fragment from pBR322, treated with Klenow, and inserted into the Klenow-treated PvuI site to produce pLOI706EH. This blunt-ended ligation destroyed the PvuI site but restored the EcoRI site at the 5' end of the tet gene. In pLOI706EH, transcription of the tet gene occurs in the same direction as the tac promoter.

RSF1010—based vectors are typically present in low copy number, as reported by Frey et ai., loc. cit. To facilitate the production of large amounts of plasmid DNA, pLOI706EH was fused at the SstI and NotI sites to plasmid pLOI142, a derivative of pUC18 that was constructed by insertion of an 8 bp NotI linker into the SmaI site of pUCl8. The resulting plasmid, pLOI707EH (12,975 bp) contains the pUC18 colE1 replicon in addition to the RSF1010 replicon, and is present at a high copy number in *E. coli* (The FIGURE). This construct, which now contains a functional bla gene (pUC18) in addition to the tet gene (Tc$^r$p$^r$), can be regarded as a double-duty vector since it can be used for insertion of a foreign gene into the RSF1010—based controllable expression vector as well as into a modified pUC18 (pLOI142).

Plasmids containing the *Z. mobilis* genes of interest were constructed using standard methods as described by Sambrook et al., MOLECULARCLONING: A LABORATORY MANUAL, 2nd ed. Cold Spring Harbor laboratory, Cold Spring Harbor, N.Y. (1989) with *E. coli* DH5α (thi lacZΔM15 recA nal$^r$) as the host, grown at 37° C. in Luria broth or on medium solidified with 15 g/liter agar. Resistance genes for tetracycline and ampicillin were used as selectable markers. Selections were made on medium containing 10 mg/liter tetracycline or 50 mg/liter ampicillin. Plasmid construction is outlined in the FIGURE.

In the FIGURE, DNA from *Z. mobilis* is indicated by stippling. Solid regions represent DNA derived from pUC18. Open regions represent DNA derived from pLOI706EH. Triangles within plasmids indicate the direction of transcription. The terminator for the glf operon is represented by a t. Pz, Ptac, and Plac represent the *Z. mobilis* glf promoter, the tac promoter, and the lac promoter, respectively. Primes are used to indicate incomplete genes. Genes encoding GLF (glf) and GLK (glk) were cloned from *Z. mobilis* on separate DNA fragments, pTC111 and pTC120, respectively. The full *Z. mobilis* glf-zwf-edd-glk operon was assembled from pTC111 and pTC120, to produce pLOI740 as shown.

Two derivatives were constructed in which frame-shift mutations were inserted into either glf or glk, by digestion with EagI or MluI, treatment with DNA polymerase I and self-ligation, to produce pLOI744 and pLOI746, respectively (not shown). A third derivative was constructed in which large parts of zwf and edd were deleted by digesting with BglII and NsiI, after conversion to blunt ends, to produce pLOI790.

Z. mobilis DNA fragments (SacI to XbaI) from these plasmids were used to replace pUC18 in pLOI707EH (SacI-XbaI), an RSF1010—based (broad-host-range) expression vector containing the tac promoter and a lacI$^q$ repressor gene according to the technique of Arfman et al. *J. Bacteriol.* 174:7370–7378 (1992). Resulting plasmids were designated pLOI742(glf zwf edd glk), pLOI763 (zwf edd glk), pLOI767 (glf zwf edd) and pLOI792 (glf glk), respectively.

The polymerase chain reaction was used to construct a derivative of pLOI142 (pUC18 containing a NotI linker in the SmaI site) which contained only the coding region and ribosomal-binding site for glf. The resulting plasmid is designated pLOI670. Primers used to construct pLOI670, 5' GCG AGC TCA AGG CGG GAG AGG AAT 3' (5' end of the glf gene) and 5' GTG GCG GCC GCC TAC TTC TGG GAG CG 3' (3' end of the glf gene), included SacI and NotI sites, respectively.

Example 2 DEMONSTRATION OF FUNCTION OF THE *Z. MOBILIS* GLUCOSE UPTAKE SYSTEM IN A GLUCOSE NEGATIVE MUTANT OF *E. COLI* USING INDICATOR PLATES AND MINIMAL MEDIUM A glucose negative mutant of *E. coli K12*, strain ZSC113 (CGSC #5457-lacZ82 ptsM12 ptsG22glk-7 rha-4 rpsL223), was obtained from the *E. coli* Genetics Stock Center (Dr. Barbara Bachmann, Yale University, New Haven). This strain was originally constructed by Curtis and Epstein, *J. Bacteriol.* 122:1189–1199 (1975). It contains mutations in glucose-specific and mannose-specific phosphotranferase genes and in glucokinase and, thus, is unable to transport or phosphorylate glucose. It is unable to grow on minimal media containing glucose and is unable to produce organic acids from glucose on complex media.

ZSC113 was grown either on Luria broth or in M9 minimal medium containing 1% glucose, trace metals and thiamin (2 mg/liter) according to Silhavy et al. Cold Spring Harbor Laboratory, Cold Spring Harbor, N.Y. (1984). This strain was transformed with the expression vectors from Example 1.

ZSC113 recombinants were tested for growth on glucose minimal medium and acid production on glucose MacConkey agar containing 2 g/liter glucose. All strains grew on this complex medium during overnight incubation at 37° C. Of the recombinants summarized in Table 1, growth on glucose minimal medium and acid production on glucose MacConkey agar were restored only by pLOI742 and pLOI792. Both of these recombinants contained GLK activity and the native genes for glf and glk.

Although expression was not fully controlled by the tac promoter and lacI$^q$, the addition of inducer increased the growth rate of these recombinants. In the presence of 1 mM IPTG, all recombinants containing native genes for both glf and glk produced acid, demonstrating the functional expression of the *Z. mobilis* glucose uptake and phosphorylation system.

TABLE 1

Growth rate and expression of *Z. mobilis* glk in recombinants of *E. coli* ZSC113[a]

| Plasmid | Active genes | IPTG[b] (mM) | GLK activity[c] (IU mg$^{-1}$) | Specific Growth Rate (h$^{-1}$) | Acid[d] |
|---|---|---|---|---|---|
| none |  | 0 | <0.01 | 0.01 | – |
| pLOI742 | glf zwf edd glk | 0 | 1.2 | 0.30 | + |
| pLOI742 | glf zwf edd glk | 1 | 1.7 | 0.53 | + |
| pLOI763 | zwf edd glk | 0 | 1.4 | 0.05 | – |
| pLOI763 | zwf edd glk | 1 | 1.4 | 0.03 | – |
| pLOI767 | glf zwf edd | 0 | <0.01 | 0.02 | – |
| pLOI767 | glf zwf edd | 1 | <0.01 | 0.02 | – |
| pLOI792 | glf glk | 0 | 0.2 | 0.16 | + |
| PLOI792 | glf glk | 1 | 1.1 | 0.53 | + |

[a]Cells were grown overnight in M9 minimal medium containing 10 g liter$^{-1}$ gluconate to prepare inocula and for biochemical analyses. Gluconate-grown cells were diluted (0.1 O.D. 550 nm) into glucose minimal mdium to measure growth rate. values represent averages from two experiments.
[b]IPTG, isopropyl β-D-thiogalactoside.
[c]GLK activity was determined as described by Doelle (1982), op. cit. and protein was estimated by the Bradford method (1976), op. cit.
[d]Acid production on glucoes MacConkey agar plates is indicated by a (+) for growth as dark red colonies; white colonies were scored as negative (–).

Mutations in zwf and edd did not prevent acid production, indicating that neither gene product is essential. Mutations in either glf or glk abolished acid production, but this could be restored by the addition of a second plasmid (pUC18-based) containing a functional copy of the damaged gene.

GLF was not observed in denaturing gels containing membranes or soluble proteins from RSF1010-based constructs. However, this protein was clearly evident as an overexpressed band (apparent $M_r$ 51,300) using membrane fractions from DH5α(pLOI670). Other low molecular weight bands also were present and may represent degradation products. The addition of pLOI670, which contains only glf, was sufficient to restore glucose utilization in ZSC113(pLOI763), but not in ZSC113(pLOI767). This confirmed that glf had been selectively inactivated.

The glucose uptake (glf) and phosphorylation genes (glk) from *Z. mobilis* functioned well in *E. coli*, and provide an alternative to the native glucose-PTS system. This was unexpected considering the differences in plasma membrane lipids between *Z. mobilis* and *E. coli*. *Z. mobilis* contains large amounts of phosphatidyl choline and an extremely high proportion of vaccenic acid. Large amounts of hopanoids are also present in *Z. mobilis* which may be needed for ethanol tolerance. In contrast, *E. coli* contains a balanced mixture of 16 and 18 carbon fatty acids, lacks phosphatidyl choline, and lacks hopanoids. Thus, it appears that the insertion and functioning of the *Z. mobilis* glucose facilitator protein is tolerant of variations in membrane lipid composition. Portable operons encoding this permease together with glk should be useful for the genetic engineering of other organisms by providing an alternative or supplemental route for glucose uptake.

What is claimed is:

1. A recombinant host bacterium which expresses heterologous DNA that encodes a functional Zymomonas glucose-facilitated diffusion protein and a functional protein that catalyzes the ATP-dependent phosphorylation of glucose.

2. A recombinant host bacterium which expresses heterologous DNA that encodes a functional glucose-facilitated diffusion protein and a functional protein that catalyzes the ATP-dependent phosphorylation of glucose, wherein said DNA encodes *Z. mobilis* glucose-facilitated diffusion protein and *Z. mobilis* glucokinase.

3. A recombinant host bacterium as claimed in claim 2, wherein said DNA is under transcriptional control of a single promoter which is endogenous to said host cell.

4. A recombinant host bacterium according to claim 2, wherein said host cell is a gram-negative bacterium.

5. A recombinant host bacterium according to claim 2, wherein said host cell is an enteric bacterium.

6. A recombinant host bacterium which expresses heterologous DNA that encodes a functional glucose-facilitated diffusion protein and a functional protein that catalyzes the ATP-dependent phosphorylation of glucose, wherein said DNA encodes *Z. mobilis* glucose-facilitated diffusion protein and *Z. mobilis* glucokinase and wherein said host cell is a strain of *Escherichia coli*.

7. A recombinant host bacterium according to claim 3, wherein said promoter is a tac promoter.

8. A recombinant host bacterium which expresses heterologous DNA that encodes a functional Zymomonas glucose-facilitated diffusion protein and a functional protein that catalyzes the ATP-dependent phosphorylation of glucose, wherein said DNA encoding glucose-facilitated diffusion protein and the protein that catalyzes the ATP-dependent phosphorylation of glucose is contained in a plasmid.

9. A recombinant host bacterium which expresses heterologous DNA that encodes functional Zymomonas glucose-facilitated diffusion protein and a functional Zymomonas glucokinase.

10. A recombinant host bacterium as claimed in claim 2, wherein said host bacterium can grow on glucose minimal medium.

\* \* \* \* \*

UNITED STATES PATENT AND TRADEMARK OFFICE
CERTIFICATE OF CORRECTION

PATENT NO. : 5,602,030
DATED : February 11, 1997
INVENTOR(S) : Lonnie Ingram, Jacob L. Snoep and Nico Arfman It is certified that error appears in the above-indentified patent and that said Letters Patent is hereby corrected as shown below:

On the title page, under item [19] and item [75], delete "Ingrahm" and insert --Ingram--.

Signed and Sealed this

Thirteenth Day of May, 1997

*Attest:*

BRUCE LEHMAN

*Attesting Officer*  *Commissioner of Patents and Trademarks*